(12) United States Patent
Brown et al.

(10) Patent No.: US 8,436,202 B2
(45) Date of Patent: May 7, 2013

(54) USE OF PRESSURE SWING ABSORPTION FOR WATER REMOVAL FROM A WET METHANOL STREAM

(76) Inventors: Christopher J Brown, Amherst, NY (US); Marion Simo, North Tonawanda, NY (US)

(*) Notice: Subject to any disclaimer, the term of this patent is extended or adjusted under 35 U.S.C. 154(b) by 0 days.

(21) Appl. No.: 13/199,095

(22) Filed: Aug. 18, 2011

(65) Prior Publication Data

US 2012/0078003 A1    Mar. 29, 2012

Related U.S. Application Data

(63) Continuation of application No. PCT/US2010/024684, filed on Feb. 19, 2010.

(60) Provisional application No. 61/153,667, filed on Feb. 19, 2009.

(51) Int. Cl.
*C07C 67/02* (2006.01)
*C07C 67/48* (2006.01)

(52) U.S. Cl.
USPC .......................................... 560/234; 560/248

(58) Field of Classification Search ................. None
See application file for complete search history.

(56) References Cited

U.S. PATENT DOCUMENTS 7,321,052 B2 * 1/2008 Miller et al. ................. 560/231

* cited by examiner

*Primary Examiner* — Karl J Puttlitz
(74) *Attorney, Agent, or Firm* — Paul T. Lavoie, Esq.

(57) ABSTRACT

The present invention includes a process to dry a feed steam containing alcohol and a small quantity of water. The process includes the step of using pressure swing adsorption to produce a first alcohol stream of substantially dehydrated alcohol and a second mixed stream of water and alcohol. The second mixed stream is distilled in a distillation column to produce a relatively purified water stream and a wet alcohol stream. The wet alcohol stream is added to the feed stream. Optionally the present invention is used to recover excess methanol from a biodiesel reactor that uses one or both of the transesterification reaction and the esterification reaction. The biodiesel reactor produces a product stream comprising fatty acid esters, water and alcohol. Water and alcohol is separated from the product stream. The alcohol is dried as noted above. Dried alcohol is recycled to one or both of the transesterification reaction and the esterification reaction.

9 Claims, 4 Drawing Sheets

USE OF PRESSURE SWING ABSORPTION FOR WATER REMOVAL FROM A WET METHANOL STREAM

CROSS-REFERENCE TO RELATED APPLICATIONS

This application claims the benefit of U.S. Provisional Application No. 61/153,667 filed Feb. 19, 2009, and is continuation of PCT/US2010/24684, both of which are incorporated herein by reference in their entirety.

BACKGROUND OF THE INVENTION

1. Field of the Invention

The present invention relates to processes for separation of alcohol and water to produce a dry alcohol stream.

2. Description of Background Art

The separation of methanol or other alcohols from water is accomplished in commercial applications primarily by distillation. While distillation separation is quite effective under the correct conditions, substantially dehydrating an alcohol from a wet methanol or other wet alcohol stream may be more complicated. When very dry methanol or other very dry alcohol is needed, the process may be inefficient. Specifically, a relatively large distillation column may be required with a larger number of distillation plates representing a high capital investment cost. There is a practical difficulty of drying methanol to a high degree of purity by distillation even for non-azeotropic forming alcohols or alcohols that don't form constant boiling mixtures with water that requires a significant heat requirement resulting in higher operation costs, too. By wet alcohol, it is meant alcohol that has no more than 7 wt. % water and at least 0.5 wt. % water, based upon the total weight of the alcohol stream. By dry alcohol, it is meant alcohol having no more than 0.5 wt. % water, based upon the total weight of the alcohol stream. Thus, in the region where a feedstock containing methanol and other alcohols has an alcohol concentration already greater than 92 wt. % and higher levels of purity are required, distillation may be prohibitively expensive. Thus, there is a need for alternative methods of drying a wet alcohol stream—including a wet methanol stream.

A process that could potentially benefit from a more efficient process for separating water from an alcohol stream is biodiesel production. Biodiesel is produced in two main reactions esterification and transesterification. Methanol and other alcohols can be used as reactants in the production of both esterification and transesterification reactions provided that they are free of water. To promote efficient conversion, these reactions require the use of substantial quantities of excess methanol and other alcohols, which have to be removed in other parts of the process.

Animal and plant fats and oils are typically made of triglycerides which are esters of free fatty acids with the trihydric alcohol, glycerol. The production of biodiesel involves a reaction called transesterification. In the transesterification process, the alcohol is deprotonated with a base to make it a stronger nucleophile. It reacts in the presence of methanol to form glycerol and three methyl esters of the fatty acids.

This reaction for transesterification is written as follows:

(Reaction 1)

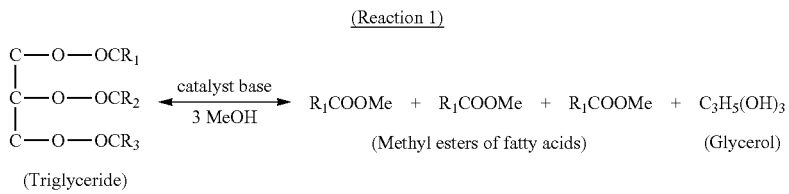

(Triglyceride)

wherein, $R_1$, $R_2$, and $R_3$ in this diagram represent long carbon chains.

The only reactants in this reaction are the triglycerides and the alcohol. The reaction is endothermic. Therefore, under normal conditions, this reaction will proceed exceedingly slowly or not at all. Application of heat and the use of a base catalyst help increase the rate of the reaction. This reaction is also a reversible reaction. Thus, higher concentrations of methanol (or other alcohol) in the reaction chamber is will result in a higher methyl ester product yield.

The excess, unreacted methanol or other alcohol required to push the reaction to greater product yield remains in the reaction mass (methyl esters and glycerol) that is produced. For economic and product quality reasons, this methanol or other alcohol must be recovered from the product stream for an economically viable use. In order to reuse this recovered methanol in a transesterification reaction, it must be dry methanol or other dry alcohol.

Excess methanol or other alcohol in the transesterification section partitions to both biodiesel (3-5 wt. % methanol to strip) and glycerin (about 25-30 wt. % methanol to strip). If water is present in this reaction, it causes the reaction to produce a larger percentage of glycerin and less biodiesel.

Furthermore, biodiesel feed stocks inevitably contain some quantity of free fatty acids. These compounds, when present in the transesterification reaction, form soaps from the FFAs by reacting with the basic catalyst and produce water as a bi-product. Free fatty acid levels in the transesterification reaction feedstock that are higher than 1% create sufficient soap and water to cause significant operational and quality problems in a biodiesel plant. Reacting the free fatty acids in a process called esterification prior to the transesterification reaction is one way to prevent soap formation in the transesterification reaction. With appropriate catalysts (such as sulfuric acid), methanol and free fatty acids react to form methyl esters of the free fatty acids. Substantial excess methanol is used in this reaction to drive the reaction towards completion and improve methyl ester product yield. Water is a byproduct of this reaction. The esterification reaction is represented by the following Reaction 2:

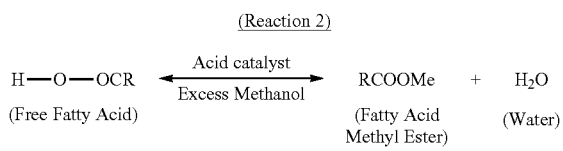

(Reaction 2)

Since water hinders the transesterification reaction, it should be removed from the product mixture following esterification but before transesterification is performed. Separating the water from the fatty acid methyl esters, oils and triglycerides can be accomplished by evaporation. But to recover the excess methanol in a dry usable form is expensive. Whatever biodiesel process is employed, removal of water from the recycled methanol or other alcohol is essential if the excess methanol or other alcohol in the product stream is to be recovered in a suitable quality for reuse in the reaction vessel.

During the recovery process of the biodiesel, methanol or other alcohol and water is removed from the biodiesel product, as a first step, resulting in a methanol or other alcohol stream that contains a concentrated level of water—about 1.5 wt. %. Presently, the typical technique for alcohol removal is either simple distillation by single stage flashing or complex distillation with a multistage distillation column.

Flashing is a very simple process and can be effective, but it does not yield a pure alcohol stream if water is present. Recycle and reuse of the alcohol in the reaction vessel is not feasible for this separation method. Multistage distillation can separate alcohol and water to a sufficiently high level of purity for recycle and reuse in the reactor, but a very large and energy intensive distillation column is required to produce the dry alcohol. A distillation column in this application is operationally challenging and is sensitive to changes in feed composition. A system that would purify alcohol, be operationally simple and be rather indifferent to feedstock composition would be a very useful for biodiesel plants. The present invention addresses these and other concerns.

SUMMARY OF THE INVENTION

The present invention represents a more efficient way of removing water from a feed stream containing alcohol and a small amount of water. By small amounts or small quantities of water, it is meant, 7 wt. % or less of water in the alcohol feed stream. The process produces highly purified, dehydrated alcohol streams. By dehydrated, it is meant no more than 0.5 wt. % water in the alcohol stream, although significantly higher levels of purity are obtainable and desired in certain aspects of the invention. The process of the present invention is particularly advantageous in a biodiesel production process. It permits efficient recovery of excess alcohol from esterification reaction and the transesterification reaction in a dehydrated state for recycle and reuse in the biodiesel production process, particularly in the transesterification reaction.

In one embodiment, there is a process to dehydrate a feed steam containing alcohol containing small quantities of water. Pressure swing adsorption is used to produce a first alcohol stream of substantially dehydrated alcohol and a second mixed stream of water and alcohol. By substantially dehydrated alcohol, it is meant alcohol containing less than 0.5 wt. %. Although, it is still considerably advantageous to produce alcohol having a water content less than 0.2 wt. %, and preferably less than 0.1 wt. % based upon the total weight of the alcohol composition. The second mixed stream is distilled in a distillation column to produce a relatively purified water stream and a third alcohol stream. By relatively pure water stream, it is meant water that is capable of being used as process water. The third alcohol stream is a wet alcohol stream and is recycled to the feed stream.

In one embodiment, the alcohol comprises methanol. Optionally, it comes from a biodiesel plant.

In another embodiment, the alcohol does not form an azeotrope or constant boiling mixture with water.

In another embodiment, the feed stream comprises less than or equal to 5 wt. % or less of water, preferably 2 wt. % or less of water.

In still another embodiment, the alcohol stream comprises about 0.3 wt. % or less of water and preferably less than 0.1 wt % or less of water.

In yet another embodiment, the pressure swing adsorption system is a pressure vacuum swing adsorption (PVSA) system which is operated during adsorption at a pressure of 65 psia or greater and preferably 100 psia or greater.

The pressure vacuum swing adsorption (PVSA) system during regeneration of the bed, of one embodiment, is operated at less than atmospheric pressure. In one embodiment, the pressure swing adsorption system is operated at a pressure of 2.5 psia or less and preferably 1 psia or less to regenerate the bed.

In one embodiment, a portion of the first alcohol stream leaving the PVSA is used to supply heat for operation of the distillation column.

In another embodiment, heat from the first alcohol stream is, optionally condensed, and is used for other process operations including heating the feed stream containing alcohol and small quantities of water or in the operation of the distillation column.

In still another embodiment, the distillation is a continuous operation. In another embodiment, the distillation is a batch operation. Typically, the pressure swing adsorption comprises at least two beds. Preferably it contains at least three beds.

Optionally or alternatively, the process comprising the additional steps of compressing the first alcohol stream to a predetermined pressure to produce a compressed alcohol stream; and In one embodiment, the process further comprises the step of condensing the first alcohol stream at the predetermined pressure in a heat exchanger with the feed stream, wherein the predetermined pressure is sufficiently high that the compressed alcohol stream vaporizes the feed stream. The process has a first alcohol stream that is fed into a biodiesel esterification or transesterification reactor to produce methyl esters or other higher esters produced from reactions with alcohols.

The process of one embodiment comprises the steps of: compressing the first alcohol stream to produce a compressed alcohol stream; and heating the bottoms of the distillation column with the compressed alcohol stream.

In one embodiment, a portion of the compressed dry alcohol is used to supply heat for distilling the mixed water alcohol stream from the pressure swing adsorption step.

In another embodiment, there is an integrated process to produce biodiesel in a biodiesel production facility. The process comprises the step of reacting biodiesel in a reactor selected from the group consisting of transesterification reactors and esterification reactors to produce a product stream comprising fatty acid esters, glycerol, water and alcohol. Alcohol and water are separated from the product stream to produce a first mixed stream containing water and alcohol. The first mixed stream is condensed and fed into a pressure vacuum swing adsorption (PVSA) system to produce a first alcohol stream a second mixed stream containing water and alcohol. The first alcohol stream is dehydrated. The second mixed stream is distilled in a distillation column to produce a relatively purified water stream and a third mixed stream containing alcohol and water. The third mixed stream is mixed with the first mixed stream and is fed into the pressure vacuum swing adsorption system. The biodiesel production process can be modified according to any of the embodiments relating to the separation of alcohol from water discussed above. Additionally, heat recovered from the first alcohol stream can be used as a heat source in any location in the biodiesel plant.

In one embodiment of the present invention, the distillation column has input flow rate that is less than or equal to the flow rate of a pressure swing adsorption system used for the step of using pressure swing adsorption. Preferably, the distillation column has input flow rate that is less than or equal to the flow rate of a pressure swing adsorption system used for the step of using pressure swing adsorption, by a factor of 0.9, more preferably by a factor of 0.7, most preferably by a factor of 0.5.

In another embodiment, the dry alcohol stream that is produced by pressure swing adsorption has a predetermined water content. The energy cost of producing a mole of the dry alcohol stream is less than the energy cost of producing a mole of alcohol having a predetermined water content by distillation. In one embodiment, the energy cost of producing a mole of the dry alcohol stream is less than the energy cost of producing a mole of alcohol having a predetermined water content by distillation by a factor of 0.9, preferably by a factor of 0.8, more preferably by a factor of 017.

The present invention, including its one or more embodiments, can be better understood with reference to the following drawings, detailed description and examples, which are included to teach and exemplify the invention without limiting the scope of the invention except as set forth in the claims.

DETAILED DESCRIPTION OF THE INVENTION

Figure 1:
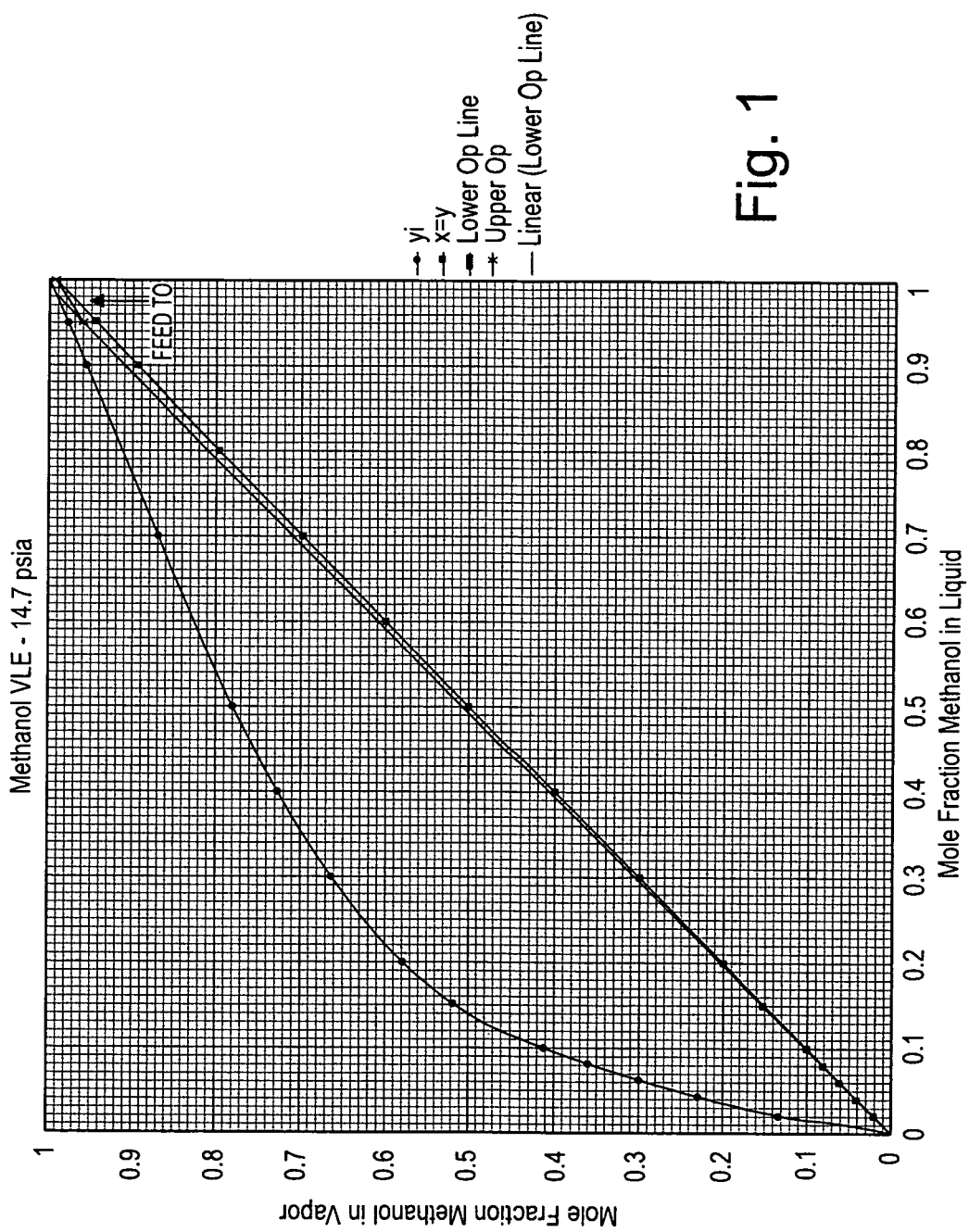
FIG. 1 is a vapor liquid equilibrium curve for the binary methanol and water at atmospheric pressure.

The present invention is a process to dehydrate a feed stream containing alcohol and water. The content of water is less than 7 wt. % of the wet alcohol feed stream. The wet alcohol feed stream is treated with a pressure swing adsorption system, preferably a pressure vacuum swing adsorption system, to produce a dry alcohol stream and a mixed stream containing water and alcohol. The dry alcohol stream can be used for process steps that require dry alcohol. The mixed stream is then distilled to produce a water stream. The overhead of the distillation step produces a wet alcohol stream which is recycled to the wet feed stream of the pressure swing adsorption system.

The wet alcohol stream preferably contains an alcohol that may or may not form an azeotrope or a constant boiling mixture with water. In one embodiment, the alcohol is propanol or isopropyl alcohol. In another embodiment, the alcohol is methanol.

As noted above, the wet alcohol stream contains less than 7 wt. % water based upon the total weight of the feed stream. Preferably, the wet alcohol stream contains less than 5 wt. %, less than 3 wt. %, less than 2 wt. % water based upon the total weight of the feed stream. The feed stream is directed into a pressure vacuum swing adsorption (PVSA) system. Prior to entering the PVSA system, the wet alcohol feed stream is vaporized. Vaporization is accomplished in one embodiment by a heat exchanger using process steam, preferably, superheated process steam. The temperature of the wet alcohol feed stream prior to entering the pressure swing adsorption system is from about 130 C to about 180 C, preferably from about 145 C to about 170 C, more preferably from about 155 to about 165. In one preferred embodiment, the temperature of the wet alcohol feed stream prior to entering the pressure swing adsorption column is 160 C. In another embodiment, the dry alcohol stream is compressed and is used at least in part to vaporize the wet alcohol feed stream. The dry alcohol stream is compressed to a pressure ranging from about 80 psia to about 180 psia, preferably from about 100 psia to about 120 psia to provide heat usable for vaporization of the wet alcohol feed stream.

In one embodiment, the pressure swing adsorption system uses a two bed system. Optionally, a three bed system is used. In another embodiment, four or more beds are used. The beds contain an adsorption medium that selectively adsorbs water into the pores of the sieve versus the alcohol from which it is to be separated. In one embodiment, the molecular sieve is a zeolite molecular sieve. In another embodiment, the pore size is less than 5 angstroms but greater than 2 angstroms. In another embodiment, the molecular sieve has a pore size of 3 angstroms. Examples of suitable molecular sieve for the separation of alcohol and water include but are not limited to 4A Zeolite and 3A Zeolite. One preferred molecular sieve for the separation of methanol and water is 3A Zeolite.

The pressure during adsorption is typically in the range from about 20 psia to about 150 psia, preferably from about 50 psia to about 140 psia, more preferably from about 60 psia to about 120 psia. In one preferred embodiment, the pressure during the adsorption process is about 85 psia.

The pressure during the regeneration or purge cycle has a minimum pressure that is typically in the range from about 0.5 psia to about 10 psia, preferably from about 1 psia to about 3 psia, more preferably from about 1.5 psia to about 3.5 psia. In one preferred embodiment, the pressure during the regeneration or purge cycle has a minimum pressure that is about 2 psia. Accordingly, in a preferred embodiment, the purge occurs under conditions below atmospheric pressure and is a pressure vacuum swing adsorption (PVSA) system.

Preferably, the cycle time of the pressure swing adsorption is defined as the duration of the adsorption portion of the pressure swing adsorption cycle. It is a minimum of 3, 7, 8 and 9 minutes and a maximum of 15, 12, 10 and 9 minutes. Most preferably the cycle time is 9 minutes.

The pressure swing adsorption system separates the alcohol into a dry alcohol stream and a mixed alcohol and water stream. The dry alcohol stream, typically, has a water content that is less than about 0.5 wt. %, preferably less than about 0.3 wt. %, most preferably less than about 0.2 wt. %, based upon the total weight of the dry alcohol stream. In one embodiment, the dry alcohol stream can be effectively produced with a water content that is about 0.1 wt. % based upon the total weight of the dry alcohol stream.

A mixed alcohol and water stream contains the water adsorbed in the pressure swing adsorption system and the dry alcohol purge gas. The fraction of alcohol in the dry alcohol stream compared to the total amount fed to the system (recovery of alcohol) is greater than 0.6, preferably greater than 0.65, and most preferably greater than 0.7. In one embodiment, the PVSA system is operated effectively to produce a fraction of alcohol recovered that is 0.74.

The mixed alcohol and water stream is distilled to produce a water stream and a wet alcohol stream. A continuous or batch distillation is alternatively employed. Typically, a continuous distillation is employed. However, if the volume of mixed alcohol and water stream is sufficiently low, a batch distillation process is optionally employed. The water stream can be used for process water. The wet alcohol stream from the overhead of the distillation column is recycled back to the wet alcohol feed stream that feeds the PSA system. The amount of water in the wet alcohol stream from the overhead of the distillation step is similar to the amount of water in the wet alcohol feed stream.

In one embodiment, the dry alcohol stream is used to supply heat for the auxiliary batch distillation apparatus or continuous distillation apparatus used on the regenerated bed waste vapor stream and has added heat recovery to minimize the energy required. By using mechanical vapor recompression of the dry alcohol stream, further energy savings is possible.

In one embodiment, the invention is used in a biodiesel plant. The biodiesel plant produces a product stream of the transesterification or esterification process. These processes produce a product stream that contains among other things, biodiesel and bi-products including glycerol, methanol and water. The recovery of biodiesel fuel produces bi-products in the product stream including glycerol, methanol and water. Methanol and water is separated from product stream and glycerol by evaporation.

Figure 2:
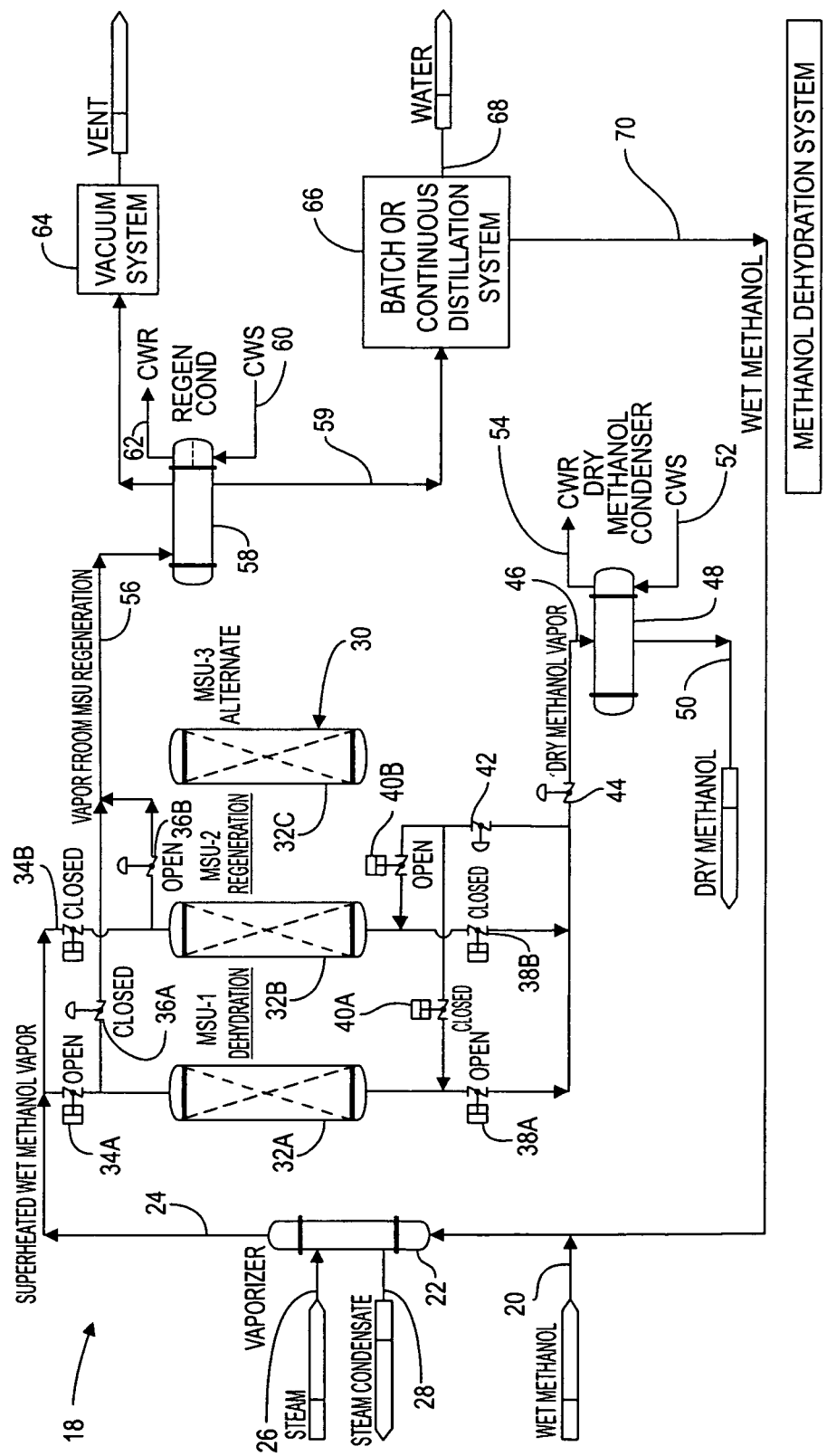
FIG. 2 is a schematic of a system for removing water from alcohol according to one embodiment of the invention.

With reference to FIG. 2, a methanol drying system 18 is disclosed according to one embodiment of the present invention. It will be understood that this system can be modified to dry other alcohols, including alcohols that do not form azeotropes with water or do not form constant boiling mixtures with water. Thus, it is understood that any discussion relating to methanol in the description of the schematic process in this specification may apply to other alcohols also. A wet methanol feed stream 20 is vaporized in a methanol vaporizer 22 heated by process steam supplied by steam feed 26 and withdrawn from the heat exchanger steam condensate stream 28. The vaporized methanol is fed along a vaporized methanol feed stream 24 into a pressure vacuum swing adsorption system 30. The pressure swing adsorption system 30 has a first molecular sieve unit 32A and a second molecular sieve unit 32B. Optionally, a third molecular sieve unit 32C may be included. However, for the sake of illustration, the fluid system is shown for a two-bed system only. A person of ordinary skill in the art will readily be able to adapt the flow diagram to accommodate a three-bed or greater bed number pressure swing adsorption system without undue experimentation.

While the first molecular sieve unit 32A is in a dehydration mode, the second molecular sieve unit 32B is in regeneration mode where the second molecular sieve unit 32B is first depressurized, then purged with the dry methanol stream and finally re-pressurized. During this part of the cycle, the first inlet valve 34A is open and the second inlet valve 34B is closed directing the vaporized wet methanol feed from line 24 into the first molecular sieve unit 32A. As the methanol passes through the molecular sieve unit 32A, water is selectively adsorbed into the pores of the molecular sieve and the dry methanol passes through a first product outlet valve 38A and master product outlet backpressure valve 44 along dry methanol stream 46. During the entire regeneration process, second product outlet valve 38B is closed to prevent flow of regenerate into the dry methanol stream 46.

Under regeneration conditions, the second molecular sieve unit 32B is first depressurized. During depressurization, both the first purge inlet valve 40A and second purge inlet valve 40B are closed to prevent purge from entering the second molecular sieve unit 32B during depressurization. The first depressurization outlet valve 36A is closed to prevent flow of the wet methanol feed steam 24 into the regenerate product line 56. The second depressurization outlet valve 36B is open allowing flow from the second molecular sieve unit 32B along regenerate product line 56. The regenerate product will contain a mixture of methanol and water. The regenerate product line is under a vacuum condition as a result of the vacuum system 64. Thus, regenerate product flows freely from the pressurized second molecular sieve unit 32B along the regenerate product line 56.

Once the second molecular sieve unit 32B is fully depressurized, the second purge inlet valve 40B is opened allowing flow of dry methanol to purge the water that is selectively adsorbed in the pores of the molecular sieve and withdraw such purge stream along regenerate product line 56 under vacuum conditions. Once the purge is completed for the second molecular sieve unit 32B, depressurization outlet valve 36B is closed while purge inlet valve 40B remains open so that dry methanol from first molecular sieve unit 32B can pressurize the second molecular sieve unit 32B to the same pressure as the first molecular sieve unit 32A.

Once the second molecular sieve unit 32B is fully pressurized, it is ready for its function to switch from regeneration to dehydration. At this point, the molecular sieve in the first molecular sieve unit 32A have selectively adsorbed a considerable amount of water. The first molecular sieve unit 32A is ready for regeneration. The two beds switch function. This occurs by the following valve changes. The first product outlet valve 38A is closed, and the first inlet valve 34A is closed, the first purge inlet valve 40A remains closed and the first depressurization outlet valve 36A is opened to begin depressurization of the first molecular sieve unit 32A.

Dehydration begins for the second molecular sieve unit 32B with the following valve arrangement. The second depressurization outlet valve 36B remains closed. The second purge inlet valve 40B is closed. The second product outlet valve 38B is opened, and the first inlet valve 34B is opened to facilitate flow from the vaporized wet methanol feed 24 into the second molecular sieve unit 32B and flow of dried methanol from the second molecular sieve unit 32B through second product outlet valve 38B and master product outlet backpressure valve 44 into dry methanol stream 46. The regeneration process as described above for the second molecular sieve unit 32B is repeated for the first molecular sieve unit 32A.

Preferably, the regeneration occurs at a pressure below atmospheric pressure under a vacuum created by the vacuum system 64. The regenerate leaves the second molecular sieve unit 32B as a vapor stream. It is cooled in a regenerate condenser 58 supplied by a cooling water source along stream 60. The cooling water is withdrawn along cooling water return stream 62.

Condensed regenerate product comprising mixed water and methanol is withdrawn along stream 59 and is fed into a batch or continuous distillation system 66. The distillation system 66 produces a bottoms stream 68 comprising purified water and an overhead stream 70 comprising wet methanol. The purified water can be used as process water in one embodiment. The wet methanol from the overhead of the distillation column is withdrawn along stream 70 and combined with stream 20 and recycled back to the pressure swing adsorption system 30.

As noted above, dry methanol product in the vapor phase is withdrawn along dry methanol stream 46. It continues into the dry methanol condenser 48. Dry methanol condenser 48 is cooled by cooling water fed along cooling water stream 52 and withdrawn from the condenser along cooling water return 54. Liquid dry methanol is removed from the dry methanol condenser 48 along line 50. The liquid dry methanol can be used as fuel to provide process heat if needed. Optionally, it can be used for any purpose dried methanol is needed.

Figure 3:
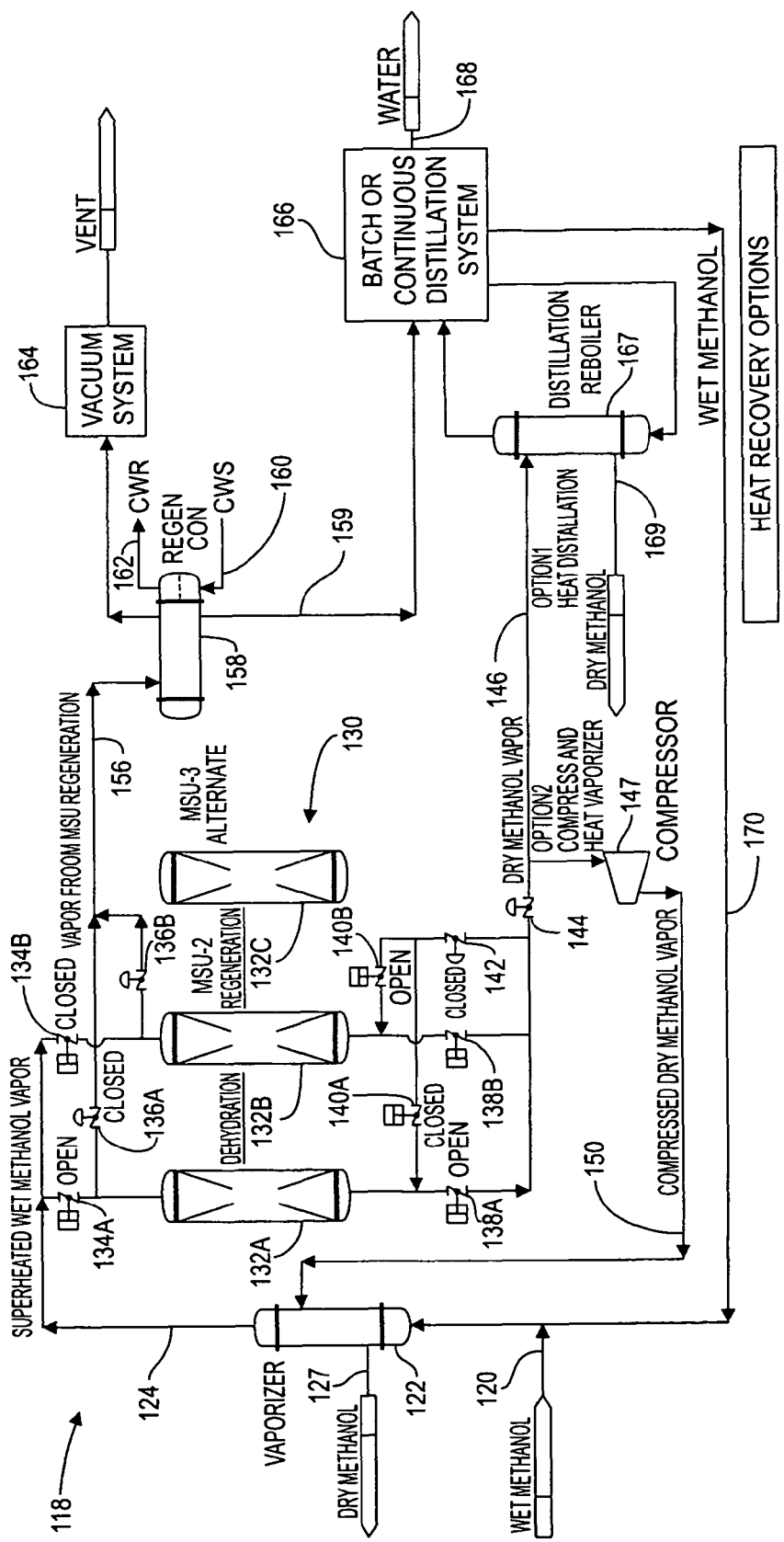
FIG. 3 is a schematic of a system for removing water from alcohol with heat recovery according to one embodiment of the invention.

With reference to FIG. 3, a methanol dehydration system 118 is shown with two heat recovery options. A wet methanol feed stream 120 is vaporized in a methanol vaporizer 122 heated by condensing, dry methanol vapor produced by the methanol dehydration system 118 and described herein below. The compressed dry methanol vapor enters the methanol vaporizer 122 by compressed, dry methanol vapor stream 150 and is withdrawn from the methanol vaporizer 122 along dry methanol liquid stream 127. The vaporized methanol is fed along vaporized wet methanol feed 124 into a pressure vacuum swing adsorption system 130. The pressure swing adsorption system 130 has a first molecular sieve unit 132A, a second molecular sieve unit 132B. Optionally, a third molecular sieve unit 132C may be included. However, for the sake of illustration, the fluid system is shown for a two-bed system only. A person of ordinary skill in the art will readily be able to adapt the flow diagram to accommodate a three-bed or greater bed number pressure swing adsorption system without unnecessary experimentation.

While the first molecular sieve unit 132A is in a dehydration mode, the second molecular sieve unit 132B is in regeneration mode. The regeneration mode includes a depressurization step, a purge step and a re-pressurization step. During dehydration, the first inlet valve 134A is open and the second inlet valve 134B is closed directing the superheated wet methanol feed from line 124 into the first molecular sieve unit 132A. As the methanol passes through the first molecular sieve unit 132A, water is selectively adsorbed into the pores of the molecular sieve and the dry methanol passes through first product outlet valve 138A and master product outlet backpressure valve 144 along dry methanol stream 146. During the entire regeneration process, second product outlet valve 138B is closed to prevent flow of regenerate into the dry methanol stream 146.

Under regeneration conditions, the second molecular sieve unit 132B is first depressurized. During depressurization, both the first purge inlet valve 140A and second purge inlet valve 140B are closed to prevent purge from entering the second molecular sieve unit 132B during depressurization. The first depressurization outlet valve 136A is closed to prevent flow of the wet methanol feed stream 124 into the regenerate product line 156. The second depressurization outlet valve 136B is open allowing flow from the second molecular sieve unit 132B along regenerate product line 156. The regenerate product comprises a mixed methanol and water stream. The regenerate product line 156 is under a vacuum condition as a result of the vacuum system 164. Thus, regenerate product flows from the pressurized second molecular sieve unit 132B along regenerate product line 156.

Once the second molecular sieve unit 132B is fully depressurized, the second purge inlet valve 140B is opened allowing flow of dry methanol to purge the water that is selectively adsorbed in the pores of the molecular sieve and withdraw such purge stream along regenerate product line 156 under vacuum conditions. Once the purge is completed for the second molecular sieve unit 132B, second depressurization outlet valve 136B is closed while second purge inlet valve 140B remains open so that dry methanol from first molecular sieve unit 132A can pressurize the second molecular sieve unit 132A to the same pressure as the first molecular sieve unit 132A.

Once the second molecular sieve unit 132B is fully pressurized, it is ready for its function to switch from regeneration mode to dehydration mode. At this point, the molecular sieve in the first molecular sieve unit 132A will have selectively adsorbed a considerable amount of water. The first molecular sieve unit 132A is then ready for regeneration. The two beds switch function. This occurs by the following valve changes. The first product outlet valve 138A is closed, and the first inlet valve 134A is closed. The first purge inlet valve 140A remains closed, and the first depressurization outlet valve 136A is opened to begin depressurization of the first molecular sieve unit 132A.

Dehydration begins for the second molecular sieve unit 132B with the following valve arrangement. The second depressurization outlet valve 136B remains closed. The second purge inlet valve 140B is closed. The second product outlet valve 138B is opened, and the first inlet valve 134B is opened to facilitate flow from the vaporized wet methanol feed 124 into the second molecular sieve unit 132B and flow of dried methanol from the second molecular sieve unit 132B through second product outlet valve 138B and master product outlet backpressure valve 144 into dry methanol stream 146. The regeneration process as described above for the second molecular sieve unit 132B is repeated for the first molecular sieve unit 132A.

Preferably, the regeneration occurs at a pressure below atmospheric pressure under a vacuum created by vacuum system 164. The regenerate leaves the second molecular sieve unit 132B as a vapor stream. It is cooled in a regenerate condenser 158 supplied by a cooling water from cooling water source stream 160 which is withdrawn from the condenser along cooling water return stream 162.

Condensed regenerate product comprising mixed water and methanol is withdrawn along stream 159 and is fed into a batch or continuous distillation system 166. The distillation system 166 produces a bottoms stream 168 comprising purified water and an overhead stream 170 comprising wet methanol. The purified water can be used as process water in one embodiment. The wet methanol from the distillation system 166 is withdrawn along stream 170 and combined with stream 120. It is recycled back to the pressure swing adsorption system 130.

As noted above, dry methanol product in the vapor phase is withdrawn along dry methanol stream 146. At this point, heat in this stream can be efficiently recovered in one of two suggested ways. First, all or a portion of the dry methanol vapor from stream 146, optionally, is directed to compressor 147 where it is compressed and fed into compressed dry methanol stream 150. As described above the compressed dry methanol stream 150 is directed into vaporizer 122 to vaporize wet methanol stream 120. The heat exchange in vaporizer 122 condenses the compressed dry methanol stream which is withdrawn from the vaporizer 122 along line 127.

Additionally or alternatively, heat may be recovered from the dry methanol vapor by directing all or a portion of the dry methanol vapor in line 146 to the distillation re-boiler 167 of the batch or continuous distillation system 166. The distillation re-boiler 167 heats the bottoms of the distillation system 166 while condensing the dry methanol vapor in line 146 which is withdrawn from the re-boiler along line 169.

Figure 4:
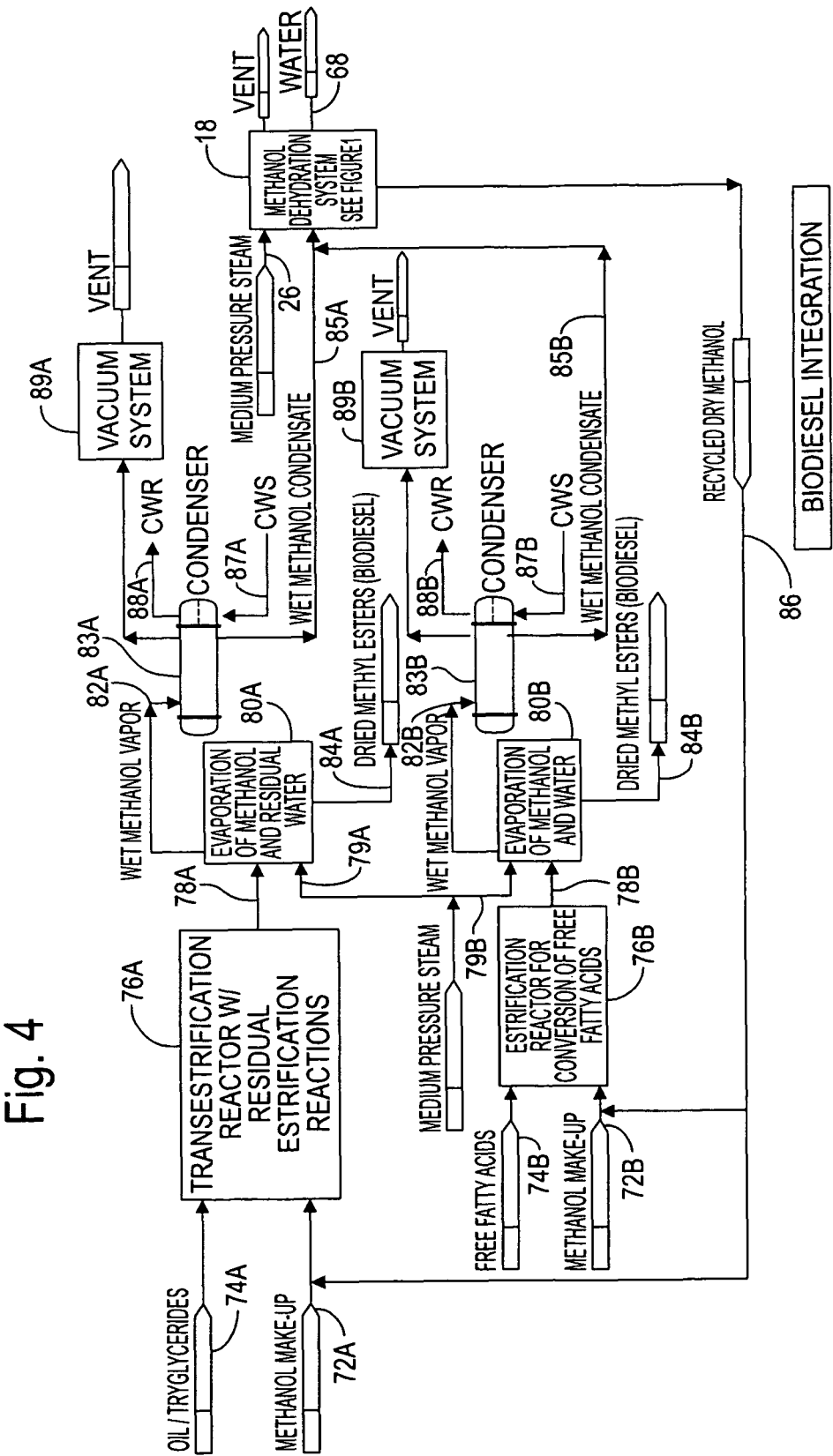
FIG. 4 is a schematic of a biodiesel plant employing the alcohol drying process according to one embodiment to efficiently recover excess methanol from the product stream in a dry form suitable to recycle to one of the biodiesel reactors.

With reference to FIG. 4, the methanol drying system of one embodiment of the present invention is integrated into a biodiesel production plant that uses either or both transesterification and esterification processes. The transesterification of oil and triglycerides occurs in a transesterification reactor 76A which is fed by oil and triglyceride feed line 74A. Optionally, the oil or triglyceride feed line was first passed through an esterification reactor such as the esterification reactor 76B to convert all free fatty acids in the triglyceride and oil feed to monoesters in a prior step to avoid formation of soap in the transesterification reaction.

Dry methanol is fed into the transesterification reactor 76A by dry methanol feed stream 72A. Methanol is supplied to the transesterification reactor 76A in a relative volume that produces a surplus of methanol during the transesterification reaction to drive the reaction towards higher yield. A base catalyst is employed in the transesterification reactor 76A and heat is applied by a source (not show) to speed the reaction. A methyl ester product stream 78A comprises fatty acid methyl esters, glycerol, water and methanol. The methyl ester product stream 78A is fed into a methanol and water evaporator. Heat applied to the methanol and water evaporator 80A by a medium pressure steam stream 79A which evaporates the methanol and water producing a wet methanol vapor. The wet methanol vapor is withdrawn through wet methanol vapor stream 82A. The evaporator 80A also produces a dried methyl ester product stream 84A comprising glycerol and dried methyl esters of fatty acids. Stream 84A is further processed to a separate biodiesel product and a purified glycerol product. Evaporation occurs under a vacuum produced by vacuum system 89A to accelerate the drying of the biodiesel.

The wet methanol vapor stream 82A is fed into condenser 83A where it is condensed by cooling water fed into the condenser along cooling water feed stream 87A which is withdrawn from the condenser along cooling water return stream 88A. A wet methanol condensate results which is sent to a methanol dehydration system via wet methanol condensate stream 85A. Optionally, wet methanol condensate in wet methanol condensate stream 85B from an esterification reaction process can be combined with the wet methanol condensate stream 85A from the transesterification process prior to methanol dehydration by the methanol dehydration system 18.

Methanol dehydration of one or more of the wet methanol condensate streams 85A and 85B occurs in system 18. The methanol dehydration is supplied by medium pressure steam along stream 26 for methanol evaporation. The methanol dehydration produces dried methanol withdrawn along dried methanol recycle stream 86 (stream 50 of system 18, FIG. 2) where it is supplied to one or more of the dry methanol feed streams 72A and 72B of the transesterification and esterification processes respectfully. Consequently, excess methanol can be recovered, dried and recycled more efficiently and cost effectively than previously known.

With continued reference to FIG. 4, the esterification of oil and triglycerides occurs in an esterification reactor 76B which is fed by free fatty acid feed line 74B. Optionally, the reactor feed line 74B supplies a mixed free fatty acid and oil or triglyceride feedstock that first converts the fatty acids to methyl esters of fatty acids in an acid catalyzed esterification reactor 76B to convert all free fatty acids in the triglyceride and oil feed 74A to monoesters before it is dried and fed into a transesterification reactor similar to transesterification reactor 76A. The advantage of such a process is to produce biodiesel from a mixed oil/triglyceride/free fatty acid containing feedstock without producing soap and compromising the biodiesel yield.

Dry methanol is fed into the esterification reactor 76B by dry methanol feed stream 72B. Methanol is supplied to the esterification reactor 76B in a relative volume that produces a surplus of methanol during the esterification reaction to drive the reaction towards higher methyl ester yield. An acid catalyst is deployed in the esterification reactor 76B and heat is applied by a source (not show) to speed the reaction. A methyl ester product stream 78B comprises fatty acid methyl esters, water and methanol. The methyl ester product stream 78B is fed into a methanol and water evaporator 80B.

Heat applied to the methanol and water evaporator 80B by a medium pressure steam stream 79B. The steam evaporates the methanol and water producing a wet methanol vapor. The wet methanol vapor is withdrawn along wet methanol vapor stream 82B. The evaporator 80B also produces a dried methyl ester product stream 84B comprising dried methyl esters of fatty acids.

If a strictly free fatty acid feedstock is used in the esterification reactor, then product stream is a biodiesel product. If a mixture of free fatty acids, oils and triglycerides feedstock is used, a dried product stream 84B may require further processing by feeding stream 84B into a transesterification reactor such as represented by 76A. Evaporation in evaporation system 80B occurs under a vacuum produced by vacuum system 89B and results in faster vaporization of the water and methanol.

In another option, it is desired to have a separate transesterification product stream 84A and esterification product stream 84B. Optionally, the wet methanol vapor stream 82A can be combined with wet methanol vapor stream 82B to eliminate redundancy of duplicate condensers 83A and 83B, vacuum systems 89A and 89B and related conduits.

The wet methanol vapor stream 82B is fed into condenser 83B where it is condensed by cooling water fed into the condenser by cooling water feed stream 87B which is withdrawn from the condenser by cooling water return stream 88B. A wet methanol condensate results which is sent to a methanol dehydration system via wet methanol condensate stream 85B. Optionally, wet methanol condensate in wet methanol condensate stream 85A from a transesterification reaction process can be combined with the wet methanol condensate stream 85B from the esterification process prior to methanol dehydration by the methanol dehydration system 18.

Dehydration of the wet methanol condensate stream 85B occurs in system 18. The methanol dehydration system 18 is heated by medium pressure steam stream 26 for methanol vaporization. The methanol dehydration produces dried methanol withdrawn along dried methanol recycle stream 86 (stream 50 of system 18, FIG. 2) where it is supplied to one or more of the dry methanol feed streams 72A and 72B of the transesterification and esterification processes, respectfully. Consequently, excess methanol can be recovered, dried and recycled more efficiently and cost effectively than previously known.

EXAMPLE 1

Comparison of the heat required to distill a methanol/water mixture versus vaporization of a comparable feed for use in pressure swing adsorption is made. Calculation of the heat required for distillation separation is made with reference to FIG. 1—the vapor liquid equilibrium (VLE) x-y diagram for methanol at atmospheric pressure. The curved line is the x-y equilibrium. The diagonal red line is x=y. A feed stream with a high methanol content limits the column operation to operating lines for the stripping section that must run very close to the x=y diagonal. Since the ratio of the molar flow of liquid methanol (L) to the molar flow of vapor methanol (V) at the bottom of the column is equal to 1.0404 (based on the simulation) and V+B=L at the bottom (where B is defined as the molar flow of bottoms), V then is equal to B/0.0404.

With a bottoms water draw of 47.17 lbmole/hr that results in 1167.57 lbmole/hr of vapor which is all water vapor and a bottoms heat input of 20,385,000 Btu/hr. So due to the operating line hugging the diagonal caused by the low water content of the feed, a very high reflux ratio is needed. Although the water removal is only 47.17 lbmole/hr, the vapor rate must be 24.75 times this. The vapor rate at the top of the column must be 2 times the product taken off the top. Thus, two times the heat required for just total vaporization of the feed is required for distillation. Half of the vapor at the top returns as reflux and half is condensed product methanol. Accordingly, to obtain dry methanol comparable water content, the straight distillation approach requires over two times the energy to vaporize the wet methanol feed. For dehydration by pressure swing vacuum adsorption, the energy required is only slightly more than that required to vaporize the wet methanol feed.

As a comparison, if we vaporize the entire feed of 785.45 lbmole/hr (24,500 lb/hr), the heat load is much less for vaporization than distillation. Methanol's latent heat is about 325 Btu/lb and water is 972 Btu/lb. The total vaporization load is 8,517,000 Btu/hr. Add perhaps 2,000,000 Btu/hr for superheating and preheating (heat recovery exchangers will be used as well) then the total load is about 10,517,000 Btu/hr or about half that of distillation. The energy savings is on the order of $860,000 per year for a system having a capacity as described above (assuming energy cost at $8.50/MMBtu/hr and continuous operation).

EXAMPLE 2

Simulations of a two-bed pressure swing adsorption system constructed according to the system disclosed in FIG. 2 were performed. Operating conditions including cycle time, absorption pressure ($P_H$), regeneration pressure ($P_L$), bed length (L), bed diameter (D), and number of cycles is also found for each case in Table 1. Simulations of this type start at an initial point and run for many cycles until a pseudo steady state is established. At about 1500 cycles, in the case of these simulations, the behavior of the beds from cycle to cycle no longer change and remain consistent. Similar simulations of a three-bed PSA system constructed according to the system disclosed in FIG. 2 were performed. Operating conditions including cycle time, absorption pressure ($P_H$), regeneration pressure ($P_L$), bed length (L), bed diameter (D), and number of cycles is also found for each case in Table 2.

Results are shown after 350 and 1500 cycles for each study. In some cases steady state was not reached after 350 cycles. Product purity, methanol recovery and concentration of regenerate are disclosed in Tables 1 and 2 as well. The amount of zeolite for both arrangements was the same and is recorded in the values for bed length (L) and bed diameter (D).

All other variables being held constant, a cycle time of 9 minutes was close to optimal. The three-bed process produced better overall results than the two bed process for a cycle time of 9 minutes. With pressure increase, product quality goes up for 9 min cycle time.

TABLE 1

Two-bed process for Pressure Swing Vacuum Absorption of Water From Methanol

| | Cycle | | | | | after 350 cycles | | after 1500 cycles | | $Y_{MeOH}$ [mol %] |
|---|---|---|---|---|---|---|---|---|---|---|
| Case # | time [min] | $P_H$ [Psia] | $P_L$ [Psia] | L [ft] | D [ft] | $Y_{H2O}$ [ppm] | Recovery [%] | $Y_{H2O}$ [ppm] | Recovery [%] | in regenerate |
| 1 | 6 | 55 | 2 | 15 | 2.5 | 20 | 70.6 | 69.6 | 70.6 | 0.2786 |
| 2 | 9 | 55 | 2 | 15 | 2.5 | 57 | 77.0 | 1904 | 76.1 | 0.3110 |
| 3 | 10.5 | 55 | 2 | 15 | 2.5 | | | 3710 | 77.9 | 0.3182 |
| 4 | 12 | 55 | 2 | 15 | 2.5 | 35970 | 85.5 | 40140 | 85.6 | 0.3208 |
| 5 | 6 | 65 | 2 | 15 | 2.5 | 6 | 69.1 | 1.3 | 69.7 | 0.2760 |
| 6 | 9 | 65 | 2 | 15 | 2.5 | 15 | 76.6 | 139 | 76.1 | 0.3169 |
| 7 | 10.5 | 65 | 2 | 15 | 2.5 | | | 23700 | 83.3 | 0.3420 |
| 8 | 12 | 65 | 2 | 15 | 2.5 | 31280 | 84.9 | 32050 | 84.9 | 0.3387 |

T

TABLE 2

Three-bed process for Pressure Swing Vacuum Absorption of Water From Methanol

| | Cycle | | | | | after 350 cycles | | after 1500 cycles | | $Y_{MeOH}$ [mol · frac] | |
|---|---|---|---|---|---|---|---|---|---|---|---|
| Case # | time [min] | $P_H$ [Psia] | $P_L$ [Psia] | L [ft] | D [ft] | $Y_{H2O}$ [ppm] | Recovery [%] | $Y_{H2O}$ [ppm] | Recovery [%] | in regenerate | |
| 1 | 6 | 55 | 2 | 10 | 2.5 | 14 | 69.3 | 4 | 69.1 | 0.2660 | −oscilating CSS |
| 2 | 7.5 | 55 | 2 | 10 | 2.5 | 27 | 73.9 | 44 | 73.7 | 0.2978 | −CSS |
| 3 | 9 | 55 | 2 | 10 | 2.5 | 64 | 76.2 | 1804 | 75.6 | 0.3071 | −CSS + breakthrough |
| 4 | 10.5 | 55 | 2 | 10 | 2.5 | 3040 | 77.4 | 4904 | 77.2 | 0.3134 | −CSS + breakthrough |

TABLE 2-continued

Three-bed process for Pressure Swing Vacuum Absorption of Water From Methanol

| Case # | Cycle time [min] | $P_H$ [Psia] | $P_L$ [Psia] | L [ft] | D [ft] | after 350 cycles $Y_{H2O}$ [ppm] | Recovery [%] | after 1500 cycles $Y_{H2O}$ [ppm] | Recovery [%] | $Y_{MeOH}$ [mol·frac] in regenerate | |
|---|---|---|---|---|---|---|---|---|---|---|---|
| 5 | 12 | 55 | 2 | 10 | 2.5 | 9700 | 78.7 | 12970 | 78.6 | 0.3113 | −CSS + breakthrough |
| 6 | 6 | 65 | 2 | 10 | 2.5 | 48 | 67.6 | 50 | 67.9 | 0.2615 | −oscilating CSS |
| 7 | 9 | 65 | 2 | 10 | 2.5 | 66 | 75.7 | 251 | 75.4 | 0.3101 | −CSS |
| 8 | 10.5 | 65 | 2 | 10 | 2.5 | 108 | 77.2 | 2715 | 76.6 | 0.3144 | −CSS |
| 9 | 12 | 65 | 2 | 10 | 2.5 | 3820 | 78.2 | 8106 | 77.9 | 0.3154 | −CSS |
| 10 | 15 | 65 | 2 | 10 | 2.5 | 19000 | 80.7 | 23180 | 80.7 | 0.3110 | −CSS + breakthrough |
| 11 | 9 | 75 | 2 | 10 | 2.5 | 14 | 74.9 | 10 | 74.9 | 0.3103 | −CSS |
| 12 | 10.5 | 75 | 2 | 10 | 2.5 | 676 | 76.2 | 919 | 76.3 | 0.3164 | −CSS |
| 13 | 12 | 75 | 2 | 10 | 2.5 | 4646 | 77.4 | 4652 | 77.4 | 0.3191 | −CSS + breakthrough |

What is claimed is:

1. A process to operate a biodiesel production facility, comprising the steps of:
   a. reacting biodiesel feedstock in a reactor selected from the group consisting of a transesterification reactor and a esterification reactor to produce a product stream comprising fatty acid esters, water and alcohol;
   b. separating alcohol and water from the product stream to produce a first mixed stream containing water and alcohol;
   c. condensing the first mixed stream;
   d. feeding the first mixed stream into a pressure swing adsorption system to produce a first alcohol stream and a second mixed stream containing water and alcohol;
   e. distilling the second mixed stream in a distillation column to produce a relatively purified water stream and a third mixed stream containing alcohol and water;
   f. combining the third mixed stream with the first mixed stream; and
   g. feeding the first mixed stream and the third mixed stream into the pressure swing adsorption system.

2. The process according to claim 1, wherein the alcohol comprises methanol.

3. The process according to claim 1, wherein the alcohol comprises an alcohol that does not form an azeotrope with water or constant boding mixture with water.

4. The process according to claim 1, wherein said first mixed stream comprises 5 wt. % water or less based upon the composition of the first mixed stream.

5. The process according to claim 1, wherein the first alcohol stream is condensed and supplies heat to the biodiesel production facility.

6. The process according to claim 1, wherein the distillation is a continuous operation.

7. The process according to claim 1, wherein the pressure-swing adsorption system comprises three molecular sieve units.

8. The process according to claim 1, further comprising the steps of:
   a. compressing the first alcohol stream to a predetermined pressure;
   b. condensing the first alcohol stream in a heat exchanger to vaporize the feed stream, wherein the predetermined pressure is sufficient to vaporize the feed stream.

9. The process according to claim 1, further comprising the step of condensing the first alcohol stream in a heat exchanger to supply heat to the distillation column.

* * * * *